United States Patent [19]

Brindle

[11] Patent Number: 5,395,666
[45] Date of Patent: Mar. 7, 1995

[54] FLEXIBLE ELASTOMERIC ARTICLE WITH ENHANCED LUBRICITY

[75] Inventor: Philip W. Brindle, Ely, England

[73] Assignee: LRC Products Ltd., London, England

[21] Appl. No.: 2,785

[22] Filed: Jan. 8, 1993

[51] Int. Cl.⁶ .......................................... A41D 19/00
[52] U.S. Cl. .................... 429/36.4; 428/323; 428/339; 428/147; 428/149; 2/168
[58] Field of Search ................ 428/35.7, 36.8, 36.9, 428/331, 339, 36.4, 323, 147, 149

[56] References Cited

U.S. PATENT DOCUMENTS

| | | |
|---|---|---|
| 2,273,995 | 2/1942 | Rogerson et al. |
| 2,976,576 | 3/1961 | Wichterle et al. |
| 3,072,914 | 1/1963 | Velonis et al. |
| 3,326,742 | 6/1967 | Shepherd |
| 3,585,103 | 6/1971 | Thomson |
| 3,607,433 | 9/1971 | Isenberg et al. |
| 3,745,042 | 7/1973 | Lim et al. |
| 3,813,695 | 6/1974 | Podell, Jr. et al. |
| 3,856,561 | 12/1974 | Esemplare et al. |
| 3,872,515 | 3/1975 | Miner et al. |
| 3,901,755 | 8/1975 | Martin et al. |
| 3,925,138 | 12/1975 | Shaul et al. |
| 3,930,076 | 12/1975 | Kliment |
| 3,940,533 | 2/1976 | Arsac |
| 3,966,530 | 6/1976 | Cutts et al. |
| 4,024,317 | 5/1977 | Stoye et al. |
| 4,070,713 | 1/1978 | Stockum |
| 4,110,495 | 8/1978 | Carter et al. |
| 4,125,477 | 11/1978 | Tani et al. |
| 4,143,109 | 3/1979 | Stockum |
| 4,302,852 | 12/1981 | Joung |
| 4,499,154 | 2/1985 | James et al. |
| 4,548,844 | 10/1985 | Podell et al. |
| 4,575,476 | 3/1986 | Podell et al. |
| 5,102,741 | 4/1992 | Miyabayashi ...................... 428/447 |

FOREIGN PATENT DOCUMENTS

| | | |
|---|---|---|
| 0543657A1 | 11/1992 | European Pat. Off. |
| 859297 | 1/1961 | United Kingdom |
| 1028446 | 5/1966 | United Kingdom |
| 1541155 | 3/1976 | United Kingdom |
| WO88/08311 | 11/1988 | WIPO |
| WO90/00890 | 2/1990 | WIPO |

OTHER PUBLICATIONS

Romberg, "Aqueous Chlorination of Natural Rubber Surfaces", A.C.S. Rubber Division, Spring Meeting 1986.
T.C.O. Noakes, Proc. Int. Rubb. Technol. Conf., Penang, Malaysia 1988.
Natural Rubber Technical Information Sheet No. 17, the Malaysian Rubber Producers' Research Association, Latex Series 1977.
D. C. Blackley, "High Polymer Latices", Palmerton Publishing Company, p. 548, 1966.
M. W. Philpott, J. Bubb. Res. Inst. Malaya. 22(5):441–449, 1969 (Compounding Natural Rubber Latex for Improved Performance.

Primary Examiner—James J. Seidleck
Assistant Examiner—Patrick R. Delaney
Attorney, Agent, or Firm—Darby & Darby

[57] ABSTRACT

This invention relates to elastomeric flexible articles (e.g., film articles) that exhibit enhanced lubricity ("slip") with respect to both dry and damp surfaces, particularly skin or other tissue of the wearer, as compared to similar articles or films that are not treated as described herein. This invention also relates to processes for making such articles or films.

29 Claims, 6 Drawing Sheets

FLEXIBLE ELASTOMERIC ARTICLE WITH ENHANCED LUBRICITY

FIELD OF THE INVENTION

This invention relates to elastomeric flexible articles (e.g., film articles) that exhibit enhanced lubricity ("slip") with respect to both dry and damp surfaces, particularly skin or other tissue of the wearer, as compared to similar articles or films that are not treated as described herein. This invention also relates to processes for making such articles or films.

BACKGROUND OF THE INVENTION

Elastomeric surfaces of articles, in general, exhibit poor lubricity with respect to a dry surface, such as dry skin or other mammalian tissue. These properties are due to surface friction. Additionally, many elastomeric articles or surfaces display poor lubricity with respect to damp surfaces.

A high surface friction coefficient is useful for many applications such as tire treads, flooring and footwear. However, these same properties are a distinct disadvantage in many other applications and especially in those applications wherein an elastomeric surface must slide on another surface, such as in the donning of gloves over dry or damp skin. This is particularly important in the use of medical gloves, such as examination gloves and surgeon's gloves. These gloves are relatively close-fitting in order to provide sensitivity. Furthermore, most surgeons don their gloves after scrubbing up and without having fully dried their hands, so that areas of their hands may be dry while other areas may be distinctly damp. Consequently, the elastomeric materials useful in such applications must exhibit concurrently enhanced lubricity with respect to dry surfaces (dry slip), enhanced lubricity with respect to damp surfaces (damp slip), as well as the requisite mechanical properties (flexibility, strength, etc.).

Conventionally, dry slip is achieved by the use of powder lubricants such as magnesium carbonate, starch and talc. However, if the hands are damp, the use of a powder is counter-productive and may actually inhibit donning. Furthermore, in surgery, there is a risk of loose powder contaminating the surgical field. These materials can also cause irritation and may be allergenic.

Chlorination of rubber has also been proposed for the purpose of reducing tackiness and decreasing the coefficient of friction of rubber. (See Romberg, "Aqueous Chlorination of Natural Rubber Surfaces", A.C.S. Rubber Division, Spring Meeting (1986); T.C.Q. Noakes, Proc. Int. Rubb. Technol. Conf., Penang, Malaysia (1988); Natural Rubber Technical Information Sheet No. 17, The Malaysian Rubber Producers' Research Association, Latex Series (1977); D. C. Blackley, "High Polymer Latices", Palmerton Publishing Company (1966), p. 548, and PCT/GB92/00171, published as WO 92 13497. However, chlorination can adversely affect the mechanical properties of flexible elastomeric articles such as rubber gloves and is better avoided for this reason. In addition, chlorination produces surfaces which have very poor damp slip.

Polymeric lubricant coatings which are bonded to the tissue-contacting glove surface or are embedded in the rubber itself have been proposed for the purpose of reducing surface friction of rubber in, for example, U.S. Pat. Nos. 3,813,695; 3,856,561; 4,070,713; 4,143,109; and 4,302,852. U.S. Pat. No. 3,813,695, in particular, describes a laminated surgical glove having a flexible outer layer and a hydrophilic plastic (hydrogel polymer) inner layer. Other articles such as catheters and bathing caps coated with hydrophilic polymers are described in U.S. Pat. Nos. 3,326,742; 3,585,103; 3,607,433; 3,745,042; 3,901,755; 3,925,138; 3,930,076; 3,940,533; 3,966,530; 4,024,317; 4,110,495; and 4,125,477 as well as British Patent Publication Nos. 1028446 and 859297.

James et al., U.S. Pat. Nos. 4,499,154 and 4,575,476, describe treating a rubber article having a coating of a lubricated hydrogel polymer (inherently providing dry slip) bonded layer, with a surfactant material, such as a quaternary ammonium cationic surfactant, or a long chain fatty amine material to improve the lubricity of the coating with respect to damp skin.

U.S. Pat. Nos. 4,143,109 and 4,070,713, and British Patent 1,541,155, propose the use on the skin-contacting surface of an elastomeric medical glove of a second layer of elastomeric material bearing partially-embedded particulate matter (crosslinked starch particles or polyethylene, or ethylene-vinyl acetate copolymer particles 5–40 microns in size). The elastomeric material forming the second layer is said to adhere to both the particles and the elastomeric glove substrate. Carboxylated styrene-butadiene latex, brominated butyl rubber and styrene-polyethylene/butylene-styrene block copolymer are disclosed as specific elastomeric materials suitable for use in forming the particle-bearing layer. The patents state that (i) the elastomeric substrate can be 125–175 microns thick; (ii) the inner layer can be 5–30 microns thick; and (iii) the particle size should be greater than the thickness of the second layer. In all the examples, however, the layer is 15 microns thick, i.e. 10% of the thickness of the laminated glove and 37.5–300% of the thickness of the particles. The resulting gloves are said to be donned easily without the use of additional lubricants, such as dusting powder. The particles described all appear to be organic, solid, essentially nonporous particles. Moreover, as far as the present inventors know, the gloves described in these patents have never been commercialized despite a felt need in the art for powder-free gloves.

It has now been discovered that the dry slip and the damp slip properties of elastomeric articles can be improved substantially by providing on the wearer-contacting surface of these articles a thin layer of an adhering binder material bearing porous, absorbent microparticles and subsequently applying a surfactant or a long chain fatty amine. Under an electron scanning microscope the microparticles appear to be coated by the binder even though they are partially protruding therefrom to give a microroughened (globular reticulated) appearance to the coating, as depicted for example in FIG. 1.

SUMMARY OF THE INVENTION

Disclosed are flexible elastomeric articles displaying slip properties with respect to damp and dry mammalian tissue comprising on their wearer-contacting surface a thin coating of an adherent binder material compatible with the elastomer, the binder being bonded to said surface and appearing to envelop porous, absorbent microparticles 4–20 microns in size, the coating constituting preferably no more than about 5% of the thickness of the article. The particles are randomly distributed on the wearer-contacting surface and appear coated with the binder, while they protrude partially from the binder surface and give the coating a substantially microroughened appearance. The coated article is then treated with a surfactant or a long-chain fatty amine.

Preferred materials include polyurethane or natural rubber as the substrate elastomer for the article. Suitable binders have a glass-transition temperature within the range from about −60° to about +30° C. Preferred binders comprise at least one of a vinyl acetate-ethylene copolymer, a vinyl acetate-ethylene acrylate copolymer, a vinyl acetate-ethylene-vinyl chloride terpolymer or a polyurethane (which may be the same as or different from the substrate). Preferred microparticles are silica particles having a size within the range of 5-12 microns. Preferably, the particles have a substantially regular shape without sharp angles or edges (e.g., a near-spherical shape). Preferred surfactants are amphoteric and cationic surfactants.

The elastomeric flexible articles include, without limitation, surgical and examination gloves.

BRIEF DESCRIPTION OF THE DRAWINGS

The invention is further described by the following Figures, which are intended to illustrate it without limiting its scope.

DETAILED DESCRIPTION OF THE INVENTION

The invention envisages flexible elastomeric articles including those adapted for use in partial or total contact with mammalian tissue, such as surgical, examination and dental gloves, condoms, bandages, catheters, ureters, sheaths, and sheath-type incontinence devices and other film articles. Furthermore, the damp/dry slip-conferring materials may be provided on one or more surfaces of the article including, but not limited to, an inner and/or an outer surface relative to the wearer, as appropriate under the circumstances of the use of each article.

For purposes of this description, the outer surface of an article and, in particular, a glove, is defined as that surface which becomes an external surface of the glove in the position of actual use when worn. The inner surface is defined as that surface which is adjacent to the skin of the wearer when worn. The reverse is true in the case of a catheter or ureter: the outer surface is the surface in contact with the wearer's tissue. To avoid ambiguity, the term "wearer-contacting" surface will be used herein. "Tissue" includes skin or epithelia without limitation.

In the present invention, the substrate elastomer of the elastomeric flexible articles may be a natural or synthetic rubber. Without limitation, examples of synthetic rubbers are polyurethane, polyacrylate, polybutylene, and silicone rubbers and block copolymers of monomers such as styrene and butadiene. Polyurethane and natural rubber are preferred, with polyurethane being most preferred. Typical thicknesses of the elastomer substrate for surgical gloves are within the range 30 to 200 microns, without limitation, with 100-150 microns being preferred.

Figure 5:
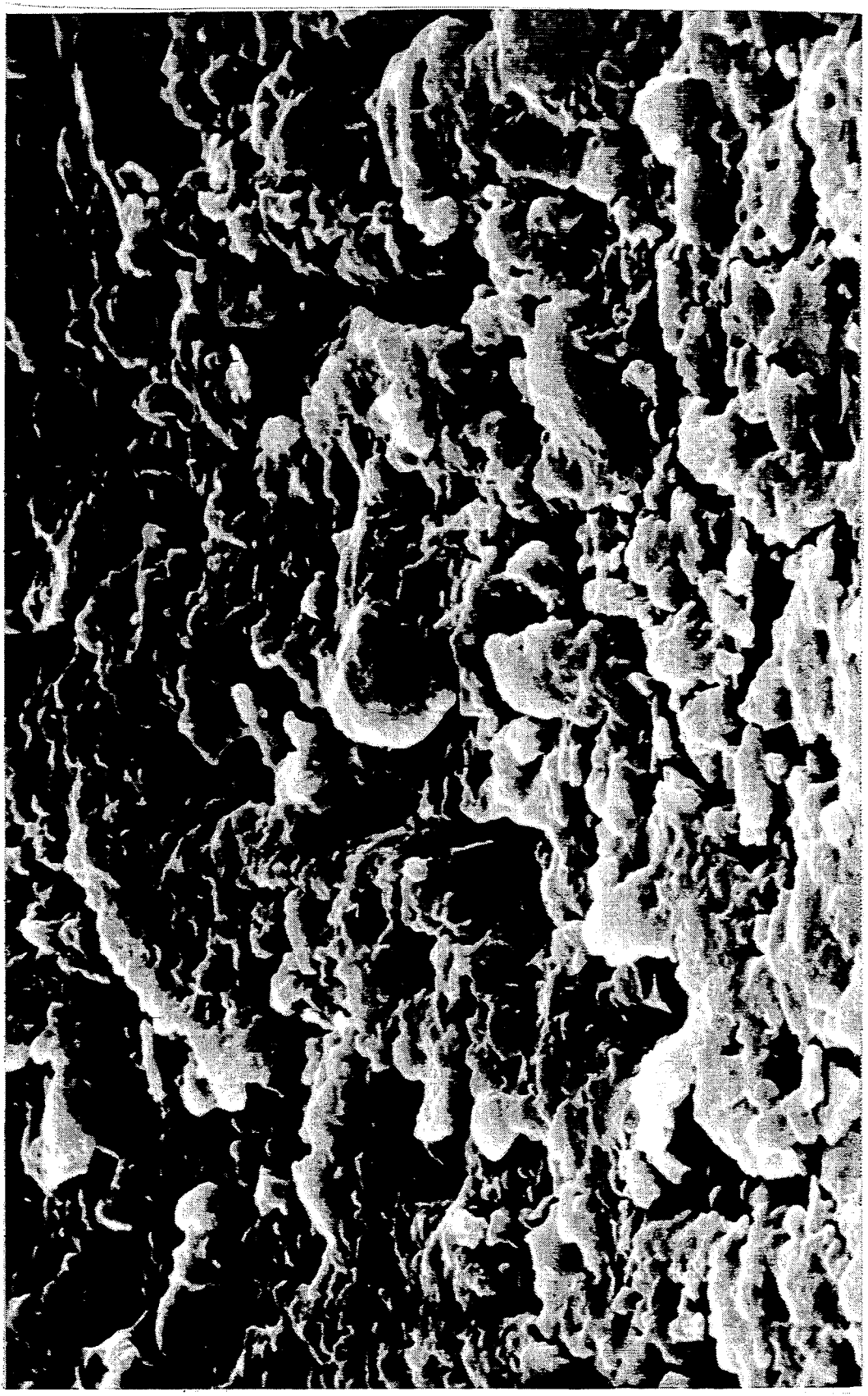
FIG. 5 is the same type of photomicrograph as FIG. 1 showing a binder layer containing corn starch microparticles according to the prior art. Noteworthy is the presence of cracks and disruptions throughout the surface.

The material used for the binder should have good adhesion to both the elastomeric substrate and to the microparticles and should preferably not adversely affect the mechanical properties of the article. Moreover, the binder layer should be resistant to the conditions of article manufacture and use. Clearly, the choice of the binder will depend, in substantial measure, on the nature of the substrate elastomer and of the microparticles. We have found, however, that by limiting the thickness of the coating relative to the thickness of the substrate and using correspondingly small, porous, absorbent microparticles, a variety of binder materials can be used. Although it is possible to obtain adequate dry-slip properties using a thicker coating and/or one that shows poor adhesion to the substrate (as deduced, for example, by the presence of a multitude of microscopic cracks in the surface—see FIG. 5), this is not desirable because such a coating shows a tendency to break up to some extent on deformation of the article (such as is incident to normal use, e.g., during donning in the case of a glove) and therefore suffers from the same disadvantages as use of powder lubricants.

When the substrate is a polyurethane and the microparticles are silica (which are preferred), the glass transition temperature of the binder polymer should be in the range of about −60° to about +30° C., preferably between about −5° and about +15° C. Preferred binder materials for a polyurethane substrate include polyurethanes, as well as copolymers and terpolymers of vinyl acetate (e.g., with ethylene, with ethylene acrylate, with ethylene and vinyl chloride, etc.).

When the substrate is natural rubber and the microparticles are silica, the glass transition temperature of the binder polymer should be in the range of about −60° to about +30° C., preferably between about −15° and about +5° C. Preferred binder materials for a natural rubber substrate include copolymers and terpolymers of vinyl acetate (e.g., with ethylene, with ethylene acrylate, with ethylene and vinyl chloride, etc.).

The microparticles are porous, absorbent microspheres, preferably made of silica, having a size within the range from about 4 to about 20 microns, preferably with at least 90% of the particles being within the range from about 5 to about 12 microns. The binder thickness should not exceed (and preferably should be less than) the mean diameter of the microparticles. For example, if the microparticle diameter is 5 to 8 microns, the preferred binder thickness is about 4-5 microns which, for a 150-micron substrate, is 2-3% of the substrate, but the coating (including the particles enveloped by it) may be as thick as about 5% of the substrate.

Microparticle porosity can be conveniently measured in terms of oil absorption (DIN ISO 787/V). Microparticles having oil absorption values higher than about 180 g/100 g and being substantially smooth (e.g., approximately spherical) in shape are suitable for the purpose of the invention, but those having oil absorption values higher than about 280 g/100 g are preferred. Examples of preferred silicas are Syloid ED5 and Syloid KD80, supplied by W.R. Grace & Co. The pore volume should be preferably in the range 1 to 2 ml/g.

A concentration of microparticles sufficient to confer dry slip properties to a glove (or other article according to the invention) is generally within the range of 10 to 40% by weight based on the binder composition. For medical gloves, this range is 15 to 30%, with 20 to 25% being preferred and 25% being most preferred. It will be appreciated by those skilled in the art that this amount is subject to optimization for a particular article according to the invention. In other words, the concentration of microparticles that will be sufficient is expected to vary, depending on (i) the application to which the flexible elastomeric article is adapted and (ii) the composition of the elastomeric article. In light of the present disclosure, however, this is within the skill of the art.

The surfactant used to endow the wearer-contacting surface with damp slip may be any surfactant which is suitable for use on skin or other tissue and does not cause an allergic, irritant, or other undesirable reaction in said skin or other tissue. Thus, in principle, amphoteric, anionic, cationic, and nonionic surfactants, and long-chain fatty amines can be used, as taught for example in various patents and patent applications recited herein, the disclosure of which is incorporated by reference in its entirety as if it were physically present in the present specification. However, in general, nonionic surfactants are found to be less effective than the other types and are not recommended as a class (although individual members of this class may be quite effective). Anionic surfactants, namely, those comprising at least one lipophilic moiety such as an alkyl, aralkyl, aryl, or cycloalkyl group containing 8 to 18 carbon atoms, and a hydrophilic moiety such as a carboxylic, phosphoric, sulfonic, sulfuric, or other acid group or salt thereof, generally provide adequate damp slip properties but such surfactants are not preferred as a class because they show a marked tendency to cause irritation to skin and tissue at concentrations effective to provide damp slip.

Suitable cationic surfactants include those comprising at least one lipophilic moiety such as an alkyl, aralkyl, aryl, or cycloalkyl group containing 6 to 18 carbon atoms, and a hydrophilic moiety such as a substituted ammonium group (for example, a tetra-alkylammonium, pyridinium, or like group). The counter-ion present should be compatible with the tissue of the wearer; it could be, for example, chloride or other halide.

Preferred cationic surfactants are quaternary ammonium compounds having at least one $C_8$–$C_{18}$ hydrocarbyl (alkyl, aryl, aralkyl or cycloalkyl) group; a preferred hydrocarbyl group is a hexadecyl group. The hydrocarbyl group may be attached to a quaternary nitrogen atom which is part of a heterocyclic ring (such as a pyridine, morpholine, or imidazoline ring).

Most preferred cationic surfactants are benzalkonium chlorides, hexadecyltrimethylammonium chloride, hexadecylpyridinium chloride, duodecylpyridinium chloride, the corresponding bromides, and a hydroxyethyl-heptadecylimidazolium halide.

Suitable amphoteric surfactants include: betaines and sulteines containing at least one $C_6$–$C_{18}$ hydrocarbyl group. Other types of suitable surfactants are amine oxides, sulfosuccinates and isethionates containing at least one $C_6$–$C_{18}$ hydrocarbyl group. Amphoteric surfactants are preferred because they generally have a low skin irritancy potential.

Mixtures of surfactants may also be used.

A particularly preferred surfactant is hexadecyl pyridinium chloride, another particularly preferred surfactant is coconut alkyldimethylammonium betaine.

In a preferred embodiment, the surfactant is bacteriocidal or bacteriostatic. The use of such a surfactant serves to inhibit bacterial growth when the layer formed on the coating is in contact with the skin or tissue of the wearer. This is especially an advantage for surgeon's gloves because they are sometimes punctured during surgical procedures, and any bacteria which may have grown on a surgeon's skin since commencement of the operation may be released into the surgical field.

When a neutral fatty amine is used, a $C_6$–$C_{18}$ hydrocarbyl group, such as a hexadecyl group, is preferably attached to the nitrogen atom. Such an amine is N-N-dimethylhexadecylamine.

The coating of surfactant or long chain fatty amine need not coat the wearer-contacting surface completely. It is only necessary that enough surfactant or long-chain amine is applied to enhance damp slip. It is preferred, to the extent that it is practicable, to keep the surfactant on the wearer-contacting surface, in the case of medical or dental gloves, in order to ensure that maximum grip is maintained on the outer surface. The surfactant can be applied as an aqueous solution containing from about 0.2 to about 2% surfactant. The article can be dipped in such solution or the solution can be sprayed or painted on it, preferably before it is removed from the former. Alternatively, the surfactant can be applied after the article is stripped from the former.

The process for applying the particle-containing coating to the wearer-contacting surface of the elastomeric substrate depends, in part, on the nature of the substrate and on whether the glove or other article is formed by dipping a former into a elastomeric polymer latex or into a solution of the elastomeric polymer in a suitable solvent. Methods for making the elastomeric substrate articles of the present invention are well-known in the art.

Where the article is formed from compounded natural rubber latex, the deposit on the former is beaded and leached in the normal way and may then be partially or fully dried but not fully vulcanized. It is envisaged that the coating will normally be applied by subsequently dipping the deposit on the former into an aqueous suspension of the coating material, i.e., the binder and microparticles. The deposit and coating may then be heated to dry them and to complete vulcanization of the rubber.

In some cases, it may be advantageous to spray or paint a suspension or solution of the coating material on to the deposit on the former. Where spraying is used, it may be convenient to spray the rubber deposit first with a suspension or solution of the binder, dry the deposit, spray with a suspension of the microparticles, dry again, and spray once more with the binder and carrier, followed by final drying and vulcanization.

Other substrate polymers in dispersed, e.g. latex, form, including polyurethanes, may be treated similarly, although a vulcanizing step will not be needed in every case, as can be readily appreciated by those skilled in the art.

When the article is formed by dipping from a polymer in solution, for example, a polyurethane in tetrahydrofuran, the deposit on the former is partially freed from solvent by heating and is then dipped into an aqueous suspension of the coating material and dried in the manner already described. In this case, also, the coating may be applied by spraying or painting, rather than dipping.

It is understood that various optional ingredients may be incorporated in these articles as apparent to those skilled in the art. For example, where the article is a glove an antiblock agent may be used which would facilitate donning and use. The antiblock agent is preferably a low-melting wax (mp. from about 100° C. to about 150° C.) such as polyethylene wax added as an aqueous emulsion (e.g., 1-2%) to the coating mixture. The particle size of the wax should be preferably less than 1 μm to avoid interference with the surface morphology.

DESCRIPTION OF THE PREFERRED EMBODIMENTS

In the following examples, which illustrate the invention without limiting its scope, the following product designations are used:

FK383 precipitated silica (Trade Mark of Degussa Ltd.)
Sipernat 50S precipitated silica (Trade Mark of Degussa Ltd.)
Silosiv A10 zeolite (Trade Mark of W.R. Grace & Co.)
Syloid AL1 silica (Trade Mark of W.R. Grace & Co.)
Syloid ED2 silica (Trade Mark of W.R. Grace & Co.)
Syloid ED5 silica (Trade Mark of W.R. Grace & Co.)
Syloid ED80 silica (Trade Mark of W.R. Grace & Co.)
Syloid 622 silica (Trade Mark of W.R. Grace & Co.)
Vinamul 3692 vinyl acetate/ethylene acrylate copolymer (Trade Mark of Vinamul Ltd. Carshalton, Surrey, England).
Vinamul 3231 vinyl acetate/ethylene copolymer (Trade Mark of Vinamul Ltd.)
Vinamul 3452 vinyl acetate/ethylene/vinyl chloride terpolymer (Trade Mark of Vinamul Ltd.)
Vinamul 3459 vinyl acetate/ethylene/vinyl chloride terpolymer (Trade Mark of Vinamul Ltd.)
Estane 5707 polyurethane (Trademark of B.F. Goodrich Inc.)
Witcobond 787 polyurethane aqueous emulsion (Trademark of Witco Chemical Corporation, New York, N.Y.).
21P40 carboxylated styrene butadiene rubber (Trademark of Doverstrand Ltd., Harlow, Essex, England).
Dehyton AB30 amphoteric surfactant (coconut alkyldimethylammonium betaine, Trade Mark of Henkel Ltd.).

The characteristics of finished films or articles were determined as follows:

Tensile strength, breaking elongation (EB), and stress at 100% strain (S100) were measured according to ASTM D412. Tear strength was measured on angle test pieces (ASTM D624).

Adhesion of the binder to the substrate and adhesion of the particles to the binder were assessed visually using a scanning electron microscope (magnification $1.5 \times 10^2$ to $2.5 \times 10^3$). The samples were evaluated visually based, respectively, on the presence and frequency of cracks in the coating and on "crater" formation in the coating (the latter indicating that particles had been dislodged and therefore did not adhere to the binder). They were then rated on an arbitrary scale from 1 to 5 with 1 signifying "excellent" and 3 signifying "barely acceptable."

Dry slip and damp slip were evaluated subjectively on a scale of 1 (excellent slip) to 5 (no slip—undonnable in the case of a glove) with 3 being "barely acceptable".

EXAMPLE 1

A film article (glove) was made by dipping a hand-shaped former into an 18% solution of a polyurethane in tetrahydrofuran (single dip process). While in the wet gel state (partially dried), and still on the former, the article was dipped into an aqueous coating solution containing 2.0% silica microparticles (Syloid ED5), 6.0% vinyl acetate/ethylene acrylate copolymer (Vinamul 3692; Tg+13° C.), 0.1% xanthan gum, and 91.9% deionized water (all percentages being by weight). It was dried for 20 minutes at 100° C. While still on the former, the dried glove was dipped into a 0.75% aqueous solution of an amphoteric surfactant (Dehyton AB30) for 10 minutes. It was then stripped from the former and air-dried. The thickness of the coating in this Example was about 5 microns; the thickness of the binder alone was 4-5 microns.

Figure 1:
FIG. 1 is a photomicrograph taken through a scanning electron microscope (SEM) showing the microparticle-bearing binder layer of a preferred embodiment of the present invention. Noteworthy is that the coating has a substantially smooth yet microroughened appearance essentially free of sharp angles, cracks and craters.

The finished glove had tensile strength 60.3 MPa and tear strength 60.1 N/mm, compared with 62.9 MPa and 59.6 N/mm respectively, for a similarly prepared but uncoated glove. Its dry slip rating was 1 and its damp slip rating 2.5. Excellent adhesion of the coating to the polyurethane (as well as of the particles to the binder) was demonstrated by scanning electron microscopy which showed a microroughened surface containing no cracks of the coating, no free fragments, and no craters (FIG. 1).

EXAMPLES 2-6

Coated polyurethane gloves were prepared as in Example 1 except that the Vinamul 3692 was substituted by one of the binders shown in Table 1, which shows the dry slip rating and degree of adhesion achieved in each case.

TABLE 1

| ADHESION OF VARIOUS BINDERS TO THE POLYURETHANE SUBSTRATE | | | |
|---|---|---|---|
| Example No. | Binder | Tg (°C.) | Adhesion |
| 2 | Vinamul 3231 | 0 | 1 |
| 3 | Vinamul 3459 | 21 | 2 |
| 4 | Vinamul 3452 | 30 | 3 |
| 5 | Witcobond 787 | −50 | 1 |
| 6 | Estane 5707 | about −40 | 1 |

EXAMPLES 7-13

Coated polyurethane gloves were prepared as in Example 1 except that the Syloid ED5 was substituted by one of the microparticles listed in Table 2 below. The dry slip ratings and degrees of adhesion achieved in each case are set forth in Table 2.

TABLE 2

EFFECT OF VARIOUS MICROPARTICLES ON PROPERTIES OF POLYURETHANE GLOVES

| Ex. No. | Particle Type | Mean Diameter | Pore Volume ml/g | Oil Adsorption g/100 g | Dry Slip | SEM |
|---|---|---|---|---|---|---|
| 1 | Syloid ED5 | 5 μm | 1.8 | 320 | 1 | FIG. 1 |
| 7 | Syloid ED80 | 8 μm | 1.8 | 300 | 1 | |
| 8 | Syloid 622 | 12 μm | 1.2 | 180 | 1.5 | |
| 9 | Syloid ED2 | 2 μm | 1.8 | 320 | 2.5 | |
| 10 | FK383 | 1–2 μm | N/A | 220 | 3 | FIG. 2 |
| 11 | Syloid AL1 | 8 μm | 0.4 | 80 | 3 | FIG. 3 |
| 12 | Sipernat 50S | 8 μm | N/A | 330 | 3.5 | |
| 13 | Corn Starch (X-linked) | 5–40 μm | N/A | N/A | 2–3 | FIG. 4 |

Figure 2:
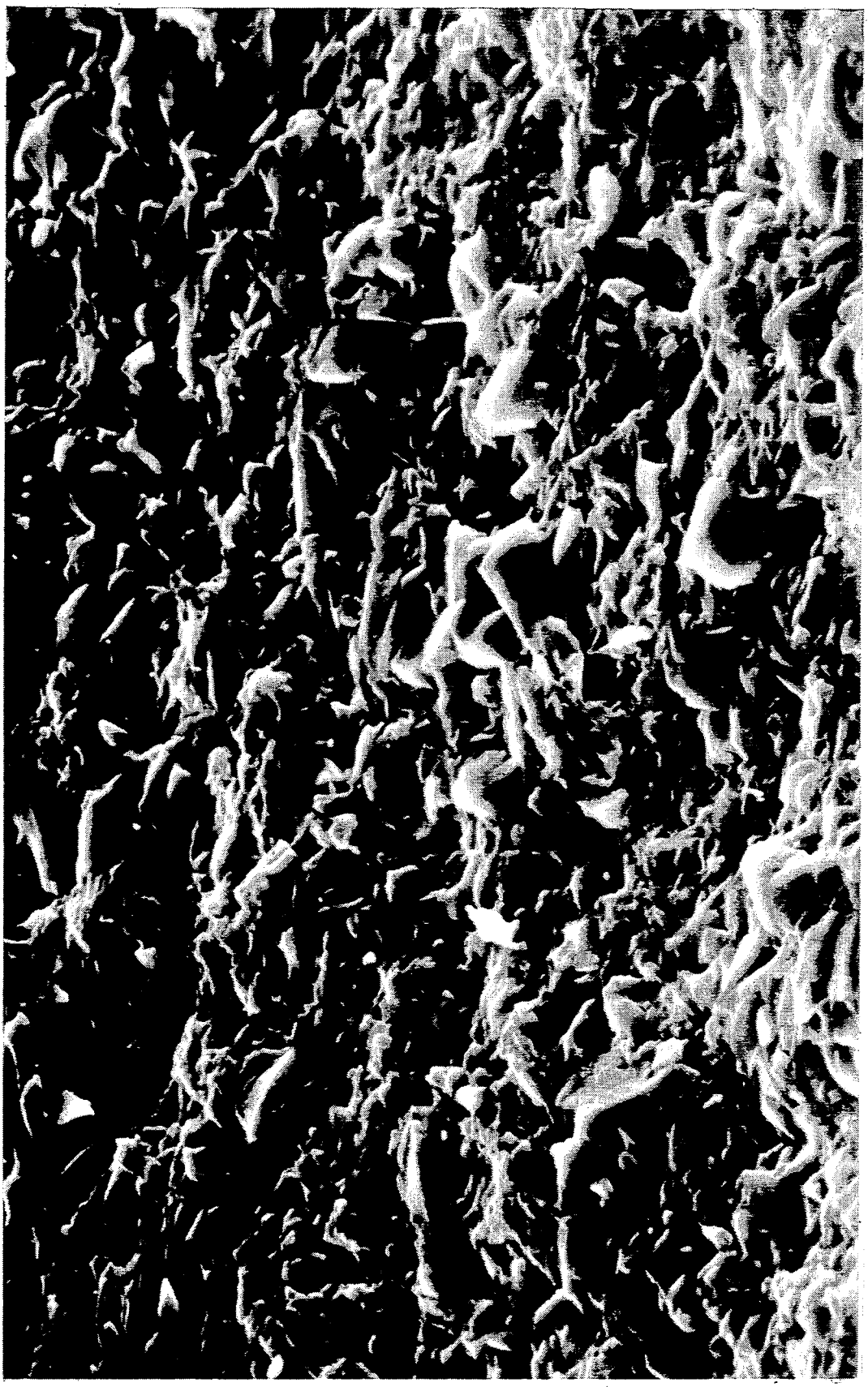
FIG. 2 is the same type of photomicrograph as FIG. 1 wherein the binder layer contains microparticles of a different type and presents sharp angles.
Figure 3:
FIG. 3 is the same type of photomicrograph as FIG. 1 containing microparticles of yet a different type and presenting a "cratered" surface.

As can be seen from Table 2, the particles in Examples 1, 7 and 8 performed most satisfactorily. Particles of Examples 9 and 10 were too small. In addition, particles of Example 10 may have been agglomerated (i.e. not of substantially smooth shape) and this may account for the highly angular appearance of the resulting coating (FIG. 2). In Example 11 the particles had insufficient oil absorption and yielded a coating with craters indicating dislodging of particles (FIG. 3). In Example 12, particle size distribution was very broad (for example, particles as large as 50 μm and as small as 1 μm were routinely seen on SEM and the proportion of 8 μm particles was relatively small), and this may account for the poor slip properties of the coating.

Figure 4:
FIG. 4 is the same type of photomicrograph as FIG. 1 showing a coating containing another type of microparticles and also presenting a cratered surface.

The corn starch particles in Example 13 also yielded a coating with craters indicating that the particles had become dislodged (FIG. 4).

EXAMPLE 14

Comparison Example

Coated polyurethane gloves were prepared as in Example 1 except that the aqueous coating dispersion contained 1.5% crosslinked corn starch, 7.5% 21P40, 0.005% xanthan gum, 0.6% casein, 0.4% zinc oxide, and 90.0% deionized water, (according to U.S. Pat. No. 4,143,109) and the dried glove was dipped into deionized water (no surfactant) for 10 minutes prior to stripping. The finished glove had satisfactory physical properties but its dry slip rating was 2–3. Adhesion of the coating to the substrate was poor, judged by its extensively cracked appearance (FIG. 5) and the fact that much of the coating had become detached during the water treatment prior to stripping. The finished glove had the appearance and feel of a powdered glove.

EXAMPLES 15–16

A glove was made from high-ammonia natural rubber latex by a procedure known to those skilled in the art and involving the steps of dipping a hand-shaped former into an aqueous coagulant, air-drying, and dipping into the latex. The wet gel deposit was then dipped into one of the coating dispersions described in Examples 1 and 2. It was then dried and vulcanized by heating for ½ hour at 120° C. The properties of the finished gloves are described in Table 3.

TABLE 3

EFFECT OF VARIOUS COATINGS ON THE PROPERTIES OF NATURAL RUBBER GLOVES

| Example No. | Coating of Example No. | Dry Slip | Adhesion |
|---|---|---|---|
| 15 | 1 | 2 | 3 |
| 16 | 2 | 2 | 1 |

Figure 6:
FIG. 6 is the same type of photomicrograph as FIG. 1 showing a coating finish similar to that of FIG. 1 on a natural rubber substrate.

As can be seen from the above Table, softer binders (i.e. binders with lower Tg) are needed to accomplish the same adhesion when a natural rubber substrate is used. FIG. 6 illustrates the adhesion and appearance of a glove according to Ex. 16. It can be seen that the finish is equivalent to that of Example 1.

EXAMPLE 17

Comparison Example

A glove was made from natural rubber latex by the method described in Examples 15–16 except that the coating was that of Example 14 (U.S. Pat. No. 4,143,109). The adhesion of this coating in the finished glove was marginally better (rated 4.5) than that of Example 14 but the slip properties and appearance were the same.

EXAMPLE 18

Aqueous Phase

A glove was made from a polyurethane emulsion (Witcobond 787) by the general method described in Examples 15 and 16, dipping the wet gel into the coating dispersion described in Example 1. The adhesion of the coating was rated 1 and dry slip was rated 1.

What is claimed is:

1. A flexible article displaying slip properties with respect to damp and dry mammalian tissue without use of powder lubricants comprising:
   a substrate layer comprising an elastomeric material, said layer having a wearer-contacting surface, said surface having a dry slip conferring coating compatible with said elastomeric material bonded thereto said coating having a thickness not exceeding about 5% of the thickness of said substrate and said coating comprising (i) a binder and (ii) porous, absorbent microparticles, said microparticles having an average diameter within the range from about 4 to about 20 microns and an oil absorption higher than about 180 g of oil per 100 g of said microparticles, said microparticles being enveloped by said binder but partially protruding therefrom thus imparting to said surface a microroughened appearance; and
   a damp slip-conferring amount of a surfactant applied to said wearer-contacting surface.

2. The article of claim 1 wherein said microparticles have a pore volume higher than 1 ml/g.

3. The article of claim 2 wherein said microparticles are made of silica.

4. The article of claim 1 wherein said microparticles are substantially regular in shape.

5. The article of claim 1 wherein said microparticles are made of silica.

6. The article of claim 1 wherein said elastomer is selected from the group consisting of natural rubber, a polyurethane, a polyacrylate, a polybutylene, a silicone rubber, and a block copolymer of styrene and butadiene.

7. The article of claim 5 wherein said binder is a polymer having a glass transition temperature higher than −60° and lower than +30°.

8. The article of claim 1 wherein said binder is selected from the group consisting of nonwater-sensitive copolymers and terpolymers of vinyl acetate with at least one of ethylene, ethylene acrylate and vinyl chloride.

9. The article of claim 1, said article being a medical glove.

10. The article of claim 1, said microparticles having a mean diameter within the range of 5–12 microns.

11. The article of claim 1, said surfactant comprising an amphoteric surfactant.

12. The article of claim 11, said surfactant being an alkyldimethylammonium betaine.

13. The article of claim 1, said surfactant being a cationic surfactant.

14. An article according to claim 13, in which said surfactant is a quaternary ammonium compound having at least one $C_6$–$C_{18}$ hydrocarbyl group.

15. An article according to claim 14, in which said hydrocarbyl group is attached to a quaternary nitrogen atom which is part of a heterocyclic ring.

16. An article according to claim 15, in which the heterocyclic ring is pyridine, morpholine or imidazoline.

17. An article according to claim 16, in which the surfactant is an N-lauryl or N-cetyl pyridinium salt, or a hydroxyethyl heptadecenyl imidazoline salt.

18. An article according to claim 14, in which said surfactant is hexadecyl trimethyl ammonium chloride.

19. An article according to claim 14, in which said surfactant is benzalkonium chloride.

20. An article according to claim 14, in which said surfactant is hexadecyl pyridinium chloride.

21. The article of claim 1, said oil absorption being higher than 280 g of oil per 100 g microparticles.

22. The article of claim 6 wherein said polyurethane is selected from the group of polyethers, polyesters, polycaprolactones, and combinations of at least two of the foregoing.

23. A flexible article displaying slip properties with respect to damp and dry mammalian tissue without the use of powder lubricants, said tissue including skin, said article comprising:

a substrate layer comprising a polyurethane elastomer, said layer having a tissue-contacting surface, said surface having a coating bonded thereto, said coating (i) having a thickness not exceeding about 5% of the thickness of said substrate and (ii) comprising an elastomeric binder compatible with said elastomer, said binder having a glass transition temperature within the range of −5° to +15° C., said binder enveloping porous silica microspheres having a mean diameter within the range of about 5 to about 12 microns, an oil absorption at least 180 g of oil per 100 g of said particles a pore volume greater than 1.0 ml/g, said microspheres partially protruding from said binder and imparting to said tissue-contacting surface a microroughened appearance and thereby conferring dry-slip properties to said surface; and a damp slip-conferring amount of a surfactant applied to said coated wearer-contacting surface, said damp and dry slip properties making the surface lubricious with respect to damp and dry tissue without the use of other lubricants.

24. The article of claim 23, said surfactant being selected from the group consisting of cationic and amphoteric surfactants.

25. The article of claim 23, said polyurethane being selected from the group of polyethers, polyesters, polycaprolactones, and combinations of at least two of the foregoing.

26. The article of claim 23, wherein at least 90% of said microspheres have a diameter within the range of about 5 to about 12 μm.

27. A flexible article displaying slip properties with respect to damp and dry mammalian tissue without use of powder lubricants comprising:

a substrate layer comprising an elastomeric material, said layer having a wearer-contacting surface, said surface having a dry slip conferring coating compatible with said elastomeric material bonded thereto and said coating comprising (i) a binder and (ii) absorbent microparticles, said microparticles having an average diameter within the range from about 4 to about 20 microns and an oil absorption higher than about 180 g of oil per 100 g of said microparticles; and a damp slip-conferring amount of a surfactant applied to said wearer-contacting surface.

28. A flexible article displaying slip properties with respect to damp and dry mammalian tissue without use of powder lubricants comprising:

a substrate layer comprising an elastomeric material, said layer having a wearer-contacting surface, said surface having a dry slip conferring coating compatible with said elastomeric material bonded thereto and said coating comprising (i) a binder and (ii) absorbent microparticles, said microparticles having an average diameter within the range from about 4 to about 20 microns and an oil absorption higher than about 180 g of oil per 100 g of said microparticles, said microparticles being enveloped by said binder but partially protruding therefrom thus imparting to said surface a microroughened appearance; and a damp slip-conferring amount of a surfactant applied to said wearer-contacting surface.

29. A flexible article displaying slip properties with respect to damp and dry mammalian tissue without use of powder lubricants comprising:

a substrate layer comprising an elastomeric material, said layer having a wearer-contacting surface, said surface having a dry slip conferring coating bonded to said elastomeric material said coating comprising (i) a binder and (ii) absorbent microparticles, said microparticles having an oil absorption higher than about 180 g of oil per 100 g of said microparticles; and a damp slip-conferring amount of a surfactant applied to said wearer-contacting surface.

* * * * *